United States Patent
Griffin, III

[11] Patent Number: 6,144,870
[45] Date of Patent: *Nov. 7, 2000

[54] CATHETER WITH IMPROVED ELECTRODES AND METHOD OF FABRICATION

[75] Inventor: Joseph C. Griffin, III, Atco, N.J.

[73] Assignee: ProCath Corporation, West Berlin, N.J.

[*] Notice: This patent issued on a continued prosecution application filed under 37 CFR 1.53(d), and is subject to the twenty year patent term provisions of 35 U.S.C. 154(a)(2).

[21] Appl. No.: 08/735,400

[22] Filed: Oct. 21, 1996

[51] Int. Cl.[7] .............................. A61B 5/04; A61N 1/05
[52] U.S. Cl. ............................ 600/374; 607/122; 29/863
[58] Field of Search .................... 600/374, 381, 600/393; 607/116, 117, 119, 122; 29/863

[56] References Cited

U.S. PATENT DOCUMENTS

| | | | |
|---|---|---|---|
| 3,769,984 | 11/1973 | Muench | 607/122 |
| 3,995,623 | 12/1976 | Blake et al. | |
| 4,444,195 | 4/1984 | Gold | 607/122 |
| 4,481,953 | 11/1984 | Gold et al. | 607/122 |
| 4,608,986 | 9/1986 | Beranek et al. | 607/123 |
| 4,777,955 | 10/1988 | Brayton et al. | 607/374 |
| 5,029,585 | 7/1991 | Lieber et al. | |
| 5,499,981 | 3/1996 | Kordis | |

*Primary Examiner*—Lee Cohen
*Attorney, Agent, or Firm*—Blank Rome Comisky & McCauley LLP; Donald R. Greene

[57] ABSTRACT

A catheter has a flexible, elongate, substantially cylindrical catheter body with at least one lumen extending from the proximal end toward the distal end. One or more radial passages intersect the lumen from the outer surface of the catheter body. A conductive lead is threaded through the lumen and passage to the outer surface of the catheter where it is circumferentially wrapped about the catheter to form a lead portion. A metal sleeve electrode is rotationally swaged over the lead portion in electrically conductive contact with the lead portion. A plurality of lead portions may be formed circumferentially about a catheter body by threading the conductive lead out of a passage around the catheter and back into the passage and lumen to another passage where another lead portion is formed.

3 Claims, 2 Drawing Sheets

CATHETER WITH IMPROVED ELECTRODES AND METHOD OF FABRICATION

FIELD OF THE INVENTION

The present invention relates generally to catheters, and more particularly to a catheter with an improved electrode structure and a method of fabricating the catheter electrodes.

BACKGROUND OF THE INVENTION

Catheters are sometimes provided with electrodes for selectively stimulating and/or sensing electrical activity in body tissue, such as the heart. For example, a catheter may be inserted into the cardiovascular system of the patient, through the superior vena cava (SVC), and into the heart so as to achieve placement of an electrode or electrodes in desired position(s) within the heart or adjacent a chamber of the heart to evoke a response of tissue to an electrical signal applied to the electrodes. The catheter is generally a hollow tube extruded from a resilient polymeric material, such as a silicone or polyurethane rubber, with one or more passages or lumens extending longitudinally through the tube. Electrodes are typically formed of annular metal bands that are disposed about the circumference of the catheter at predetermined, axially-spaced locations between the proximal and distal ends of the catheter. Conductive leads pass through one or more of the lumens from the proximal end of the catheter to the more distal locations of the electrodes and are electrically connected to the metal bands, e.g., by soldering, welding or the like. An example of such catheter electrodes is disclosed in U.S. Pat. No. 3,995,623.

It is important that the conductive leads be reliably electrically connected to the metal band electrodes to insure safe and proper operation of the catheter after it has been inserted into or implanted in the body of a patient. Reliable electrical connections are especially critical in the case of catheters which have a plurality of electrodes and catheters which are bent and flexed so as to be maneuvered through sometimes twisted and tortuous body lumens, such as the vascular system including the heart. Failure of the electrical connection to a catheter electrode in such circumstances can have catastrophic consequences for a patient, especially, for instance, in the case of electrodes in temporary or implantable defibrillation catheters such as the defibrillation catheter disclosed in copending U.S. patent application Ser. No. 08/625,872 filed Apr. 1, 1996 and assigned to the assignee of the present invention, the entire disclosure of which is incorporated herein by reference.

It is therefore a principal objective of the present invention to provide a catheter with one or a plurality of electrodes which has reliable electrical connections to a conductive lead or leads extending through the catheter from the electrodes to the proximal end of the catheter and a method of fabricating the catheter in a cost effective manufacturing process.

SUMMARY OF THE INVENTION

Briefly described, according to the present invention, a catheter is provided in which a continuous conductive lead, such as a stainless steel, copper, or copper alloy magnet wire, is threaded into a lumen of the catheter tubing to the proximal end thereof via a radial hole or passage formed in the catheter wall and intersecting the lumen. The wire is snugly wrapped completely circumferentially about the catheter tubing at the location of the radial passage and tied off or looped about itself at the passage. A metal band or sleeve having an inside diameter equal to or greater than the outside diameter of the catheter tubing and circumferentially wrapped wire is slid axially along the tubing to a position substantially centered over the circumferentially wrapped wire and crimped at one end to temporarily secure the sleeve to the tubing. Thereafter, the metal sleeve is rotationally swaged to the catheter tubing so that the outer diameter of the sleeve is substantially the same as the outer diameter of the catheter tubing.

It has been found that the mechanical rotary swaging of the metal sleeve tightly against the substantially 360° circumferential wire wrap makes a reliable electrical connection between the metal sleeve and the wire conductor even under conditions of severe bending and flexing of the catheter during use. If desired, a conductive material, such as a conductive paste or sealant, may be applied between the metal sleeve and the catheter tubing prior to rotationally swaging the sleeve in place. The metal sleeve is preferably made of a platinum alloy, such as a 90% platinum-10% iridium alloy, but may be more economically made from an electrically conductive stainless steel, such as 304 stainless steel.

A catheter having a plurality of electrodes electrically connected together in a common array is constructed according to the invention by providing a plurality of axially spaced radial passages intersecting a lumen in the catheter tubing. After forming a first circumferential wire wrap at the most proximally located first one of the radial passages, the wire is threaded back into the lumen via that passage and fed axially through the lumen to exit at the next more distally located second radial passage. The wire is then snugly wrapped circumferentially about the tubing at the second radial passage and either tied off or looped about itself if there are only two electrodes in the array, or threaded back into the lumen via the second radial passage and fed axially to the next more distally located third radial passage where the process is repeated. At the last most distally located radial passage of the array the wire conductor is tied off or looped about itself as described above. A plurality of metal sleeves is then slid axially onto the catheter tubing. Each sleeve is positioned substantially centered over a respective circumferential wire wrap and crimped to secure the same to the tubing at the proper location. The sleeves are then rotationally swaged to the catheter one by one to complete the electrode array.

A catheter may be provided with a combination of single electrodes and electrode arrays fabricated according to the method of the invention. Catheters incorporating electrodes made according to the invention may be used for any appropriate application, including mapping, defibrillation, pacing, sensing or other procedures.

Accordingly, another objective of the invention is to provide a catheter with an electrode structure having a reliable electrical connection between a single metal electrode and its external lead at the proximal end of the catheter and between the individual electrodes of an electrode array and their common external lead at the proximal end of the catheter.

BRIEF DESCRIPTION OF THE DRAWINGS

The above and still further aims, objects, aspects, features, and attendant advantages of the present invention will be better understood by consideration of the following detailed description of the presently contemplated best mode of practicing the invention, with reference to certain preferred embodiments and methods of fabrication thereof.

DETAILED DESCRIPTION OF THE PRESENTLY PREFERRED EMBODIMENT AND METHOD

Figure 1:
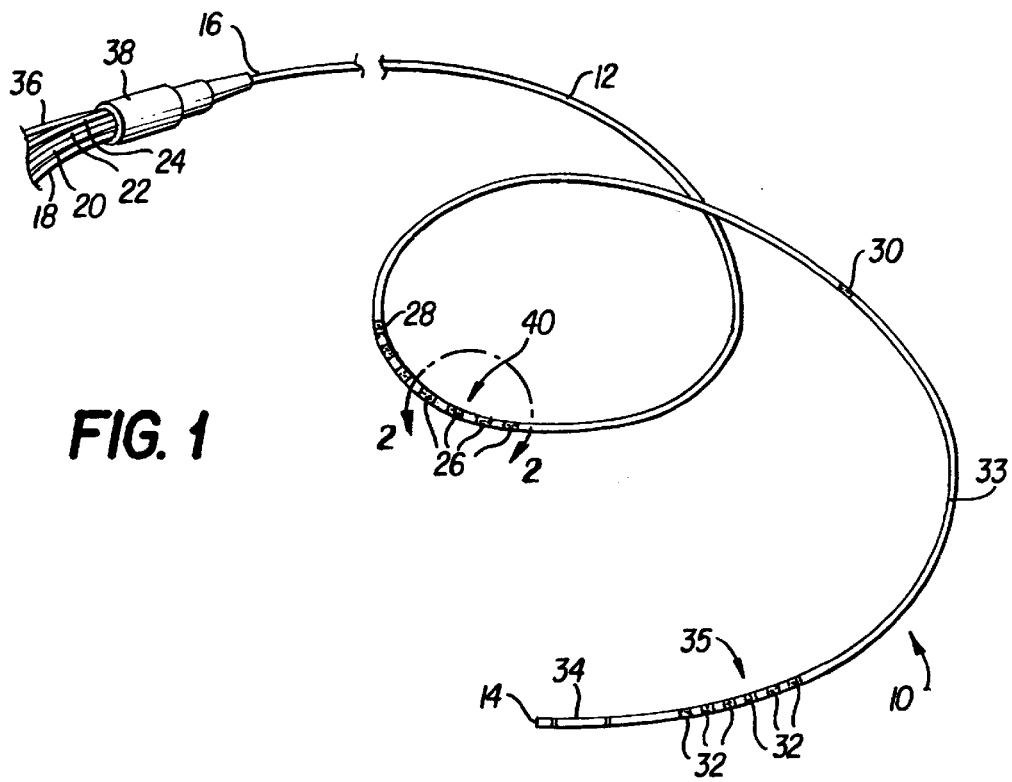
FIG. 1 is a perspective view of a catheter having a plurality of electrodes fabricated according to the method of the present invention.

Referring to FIG. 1, there is shown a catheter made according to the invention and designated generally by reference numeral 10. Catheter 10 comprises a flexible, elongate, substantially cylindrical body 12 made of an electrically insulative tubular polymeric material, such as polyurethane. The catheter body 12 has a distal end 14 and a proximal end 16 and is typically extruded with one or more lumens or passages extending between the distal and proximal ends thereof. A plurality of electrically conductive leads 18, 20, 22, 24 extend longitudinally through at least a portion of the catheter body and are electrically connected at their proximal ends to separate respective electrical connectors (not shown) of conventional construction. Preferably, each of connectors includes a respective gold-plated contact pin for electrical connection to a respective female connector (not shown). The conductive leads 18, 20, 22, 24 may be extruded into the polymeric body 12 of the catheter or subsequently inserted into respective ones of the lumens provided to accommodate the leads, in either case to predetermined portions of the length of the catheter body.

A plurality of electrodes 26, 28, 30, 32 is secured to the outer cylindrical surface 33 of the catheter body and each electrode is electrically connected to one of the conductive leads 18, 20, 22, 24 as described in more detail hereinafter. An inflatable balloon 34 is attached to the distal end 14 of the catheter body and is inflated by means of an inflation tube 36 connected to one of the lumens provided in the catheter body. Inflation tube 36 and conductive leads 18–24 are sealed to the proximal end 16 of the catheter body by means of fitting 38 in a conventional manner.

The catheter 10 shown in FIG. 1 is suitable for use as a temporary atrial defibrillation catheter of the type described in the aforementioned U.S. patent application Ser. No. 08/625,872. It is to be understood, however, that the present invention may be embodied in many different types of catheters with one or more electrodes or electrode arrays and is not to be limited by the specific embodiment shown in FIG.1.

Figure 2:
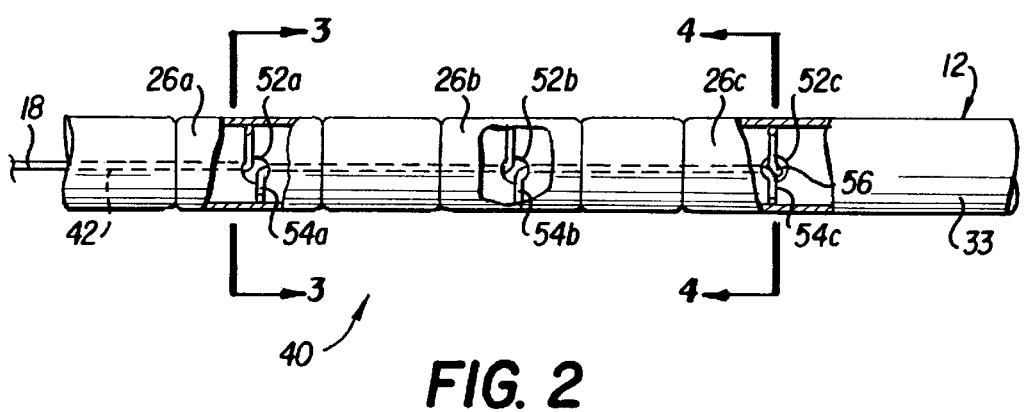
FIG. 2 is an enlarged detail view, partly fragmentary, of section 2—2 of FIG. 1 showing an electrode array of the catheter according to the invention.
Figure 3:
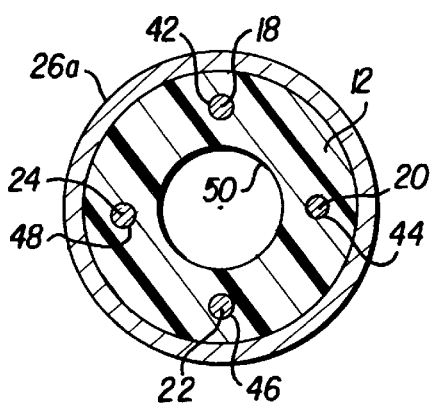
FIG. 3 is a cross-sectional view taken along line 3—3 of FIG. 2 of the catheter according to the invention.
Figure 4:
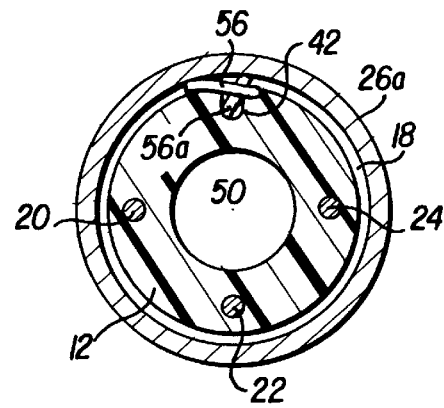
FIG. 4 is a cross-sectional view taken along line 4—4 of FIG. 2 of the catheter according to the invention.

FIGS. 2–4 illustrate the details of an electrode array 40 of the catheter 10 of the invention. Three electrodes 26a, 26b, 26c of the electrode array associated with conductive lead 18 are shown for illustrative purposes. As shown in FIG. 3, the catheter body 12 is formed with four small diameter lumens 42, 44, 46, 48 spaced 90° apart about a central inflation lumen 50 which is connected to inflation tube 36 at the proximal end 16 of the catheter body.

Each of the conductive leads 18–24 is fed through a respective lumen 42–48 and is electrically connected to a respective electrode or electrode array. In the embodiment shown, for example, conductive lead 18 is electrically connected to the electrodes 26 of defibrillation electrode array 40; conductive lead 20 is electrically connected to a single pacing electrode 28; conductive lead 22 is electrically connected to another single pacing lead 30; and conductive lead 24 is electrically connected to the electrodes 32 of defibrillation electrode array 35.

Referring again to FIG. 2, conductive lead 18 is fed or threaded through its respective lumen 42 from the proximal end thereof by means of a pull wire (not shown) connected to the distal end of conductive lead 18 and exiting from the most proximally located radial hole or passage 52a of radial passages 52a, 52b, 52c which intersect lumen 42 via openings on the outer surface 33 of the catheter body. After lead 18 has been pulled through lumen 42 and out of passage 52a, it is threaded through the eye of a needle (not shown). Lead 18 is then snugly wrapped about catheter body 12 forming a generally circular lead portion 54a having a circumferential extent of about 360°. The needle is threaded back into passage 52a and lumen 42 toward the next distally located passage 52b where it is pulled out of such passage with lead 18 attached. Lead 18 is then snugly wrapped about the catheter body to form a second generally circular lead portion 54b. That procedure is repeated at the next more distally located radial passage 52c at the end of the electrode array 40. Instead of threading the lead 18 back into passage 52c, the lead portion 54c is passed beneath the lead 18 where it exits passage 52c to tie or secure it in place at loop 56. Any excess of lead 18 is cut off at the loop 56.

Conductive lead 18 may be a conductive stainless steel, copper or copper alloy wire. If the wire is an insulated magnet wire, the insulation at the lead portions 54a–54c is stripped away to bare the metal of the wire at those locations. Preferably, the wire is drawn sufficiently tightly about the polymeric catheter body to embed or "countersink" the wire into the catheter body so that the outermost wire surface is substantially flush with the cylindrical outer surface 33 of the catheter body. The catheter body and/or the wire may be heated to facilitate embedment of the wire into the body.

It should be appreciated that for the single pacing electrodes 28 and 30, only one radial passage is necessary for a single lead portion corresponding to the lead portion 54c and the loop 56 to tie off or secure the lead portion in the manner shown in FIGS. 2 and 4. It should also be understood that for specific catheter embodiments only one or any number of electrodes may be connected to a single conductive lead with the one or the most distally located electrode of an array being fabricated as electrode 26c.

After completion of all the conductive leads 18–24, electrodes 26a–26c comprising conductive metal sleeves are secured over a respective lead portion 54a–54c in electrically conductive contact therewith. The metal sleeves are preferably a 90% platinum-10% iridium alloy composition but may be an electrically conductive 304 stainless steel or any other suitable metal or metal alloy. Stainless steel is preferred from a cost standpoint.

Figure 5:
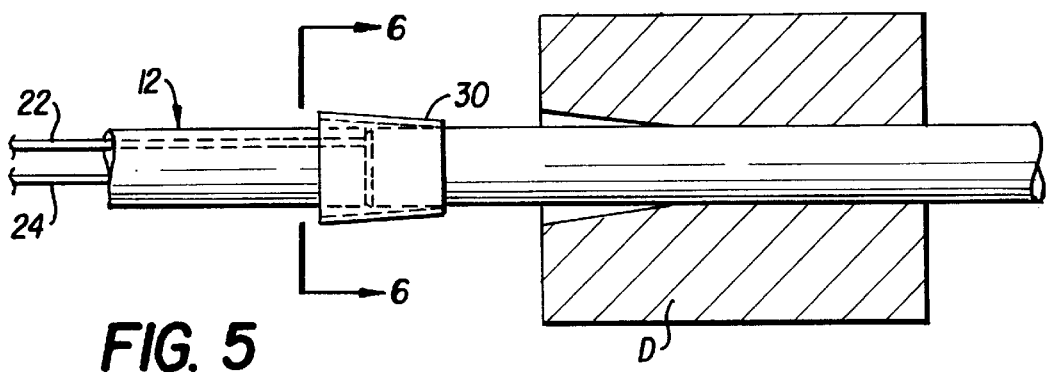
FIG. 5 is a fragmentary side view, partly in cross-section, showing one aspect of the method of fabricating a catheter according to the invention.
Figure 6:
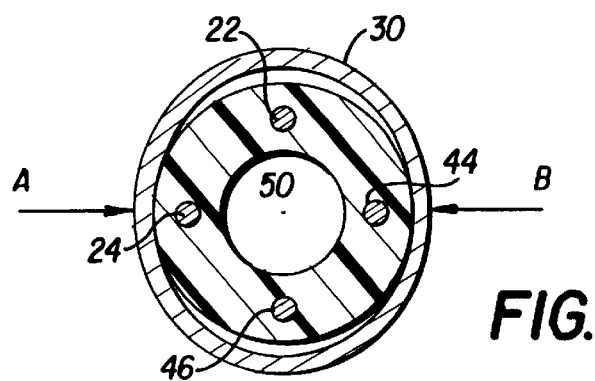
FIG. 6 is a cross-sectional view taken along line 5—5 of FIG. 5.

FIGS. 5 and 6 illustrate the method by which the metal sleeves of the electrodes are attached to the catheter body so as to electrically connect the metal sleeves to the conductive leads. After the conductive leads have been threaded into their respective lumens and the lead portions have been stripped of insulation, if any, a plurality of metal sleeves corresponding to the electrodes 26, 28, 30, 32 and having an inside diameter equal to or greater than the outside diameter of the catheter body are threaded onto the catheter body from one end or the other. The electrode sleeves are then diametrically crimped at the proximal end thereof as shown by the arrows A, B in FIG. 6 to cause the sleeve to grip the catheter body and thus secure the sleeve in place. The catheter 10 is then passed through one or more rotary dies D of a conventional rotary swaging apparatus (not shown) to rotationally swage the metal sleeve to an outside diameter substantially the same as the outside diameter of the catheter body 12 (FIG. 2). One conventional swaging apparatus that can be employed to perform the swaging operation according to the invention is a two die rotary swaging machine, Model No. NF-2 made by the Fenn Manufacturing Company of Norwalk, Conn.

It has been found that an effective and reliable electrical connection can be made between the circumferential lead portions of the conductive leads and the metal sleeves by the above-described rotary swaging process.

While preferred forms and arrangements have been shown in illustrating the invention, it is to be understood that various changes and modifications may be made without departing from the spirit and scope of this disclosure.

What is claimed is:

1. A catheter comprising:

a flexible, elongate catheter body having a proximal end and a distal end and a substantially cylindrical outer surface, a lumen extending longitudinally from the proximal end toward the distal end, a first passage in said body intersecting said lumen and having a first opening at said outer surface at a first given longitudinal location relative to the proximal end, and a second passage intersecting said lumen at a second given location further from said proximal end and longitudinally spaced from said first given location, said second passage having a second opening at said outer surface;

an electrically conductive lead extending through said lumen from the proximal end of the catheter body through said first passage and out of said first opening, a first portion of said lead extending circumferentially about the cylindrical outer surface of the catheter body, said electrically conductive lead extending from said first lead portion back into said first opening and through said lumen and said second passage and out of said second opening, a second portion of said lead extending circumferentially about the cylindrical outer surface of the catheter body and looped about itself at said second given location, said first and second lead portions each having a circumferential extent of about 360°; and a first electrode comprising a first metal sleeve disposed circumferentially about said catheter body at said first given location in electrically conductive contact with said first lead portion, and a second electrode comprising a second metal sleeve disposed circumferentially about said catheter body at said second given location in electrically conductive contact with said second lead portion, each of said first and second metal sleeves having a cylindrical outer surface and being rotationally swaged onto said catheter body over said first and second lead portions, respectively, to embed each of said lead portions into the catheter body so that said cylindrical outer surface of each of the metal sleeves is substantially flush with the cylindrical outer surface of the catheter body.

2. A method of fabricating a catheter, comprising the steps of:

providing a flexible, elongate catheter body having a proximal end and a distal end and a substantially cylindrical outer surface, a lumen extending longitudinally from the proximal end toward the distal end, and a plurality of longitudinally spaced passages in said catheter body intersecting said lumen, said passages having respective openings at said outer surface of the catheter body;

threading an electrically conductive lead through said lumen, said passages and said respective openings, and wrapping a portion of said lead circumferentially about the outer surface of the catheter body adjacent said respective openings, including guiding said conductive lead from said lumen out of one passage and its opening as a respective lead portion wrapped circumferentially about the outer surface of said catheter body, and then back into said one passage and through said lumen to the next longitudinally spaced passage and repeating said guiding step at each of the next succeeding passages; and securing a respective one of a plurality of electrodes each comprising a metal sleeve to said catheter body over and in electrically conductive contact with a lead portion at respective openings of said passages, including rotationally swaging each metal sleeve to the catheter body to embed the respective lead portion into the cylindrical outer surface of the catheter body such that the outermost surface of each said lead portion and its respective metal sleeve is substantially flush with the cylindrical outer surface of the catheter body.

3. The method of claim 2, including the step of looping the respective lead portion about itself at the opening of the last passage adjacent the distal end of the catheter body after wrapping the last-mentioned lead portion circumferentially about the outer surface thereof to secure said lead to the catheter body before swaging a respective metal sleeve thereon.

* * * * *